United States Patent [19]

Tsujino et al.

[11] Patent Number: 5,515,857
[45] Date of Patent: May 14, 1996

[54] ULTRASONIC DIAGNOSTIC APPARATUS

[75] Inventors: Hiroyuki Tsujino; Eiichi Shiki, both of Ootawara, Japan

[73] Assignee: Kabushiki Kaisha Toshiba, Kawasaki, Japan

[21] Appl. No.: 266,620

[22] Filed: Jun. 28, 1994

[30] Foreign Application Priority Data

Jul. 9, 1993 [JP] Japan ................................ 5-170435

[51] Int. Cl.⁶ ..................................................... A61B 8/06
[52] U.S. Cl. ........................................................ 128/661.1
[58] Field of Search ........... 128/660.05, 661.08–661.10; 73/861.25

[56] References Cited

U.S. PATENT DOCUMENTS

| | | | |
|---|---|---|---|
| 4,370,985 | 2/1983 | Takeichi et al. | 128/661.1 |
| 4,476,874 | 10/1984 | Taenzer et al. | 128/660.05 |
| 4,501,279 | 2/1985 | Seo | 128/661.1 |
| 4,790,322 | 12/1988 | Iinuma | 128/661.1 |
| 4,991,589 | 2/1991 | Hongo et al. | 128/661.09 |
| 5,280,787 | 1/1994 | Wilson et al. | 128/661.1 |
| 5,379,771 | 1/1995 | Kawasaki et al. | 128/661.1 |
| 5,425,365 | 6/1995 | Iinuma | 128/660.05 |

*Primary Examiner*—Francis Jaworski
*Attorney, Agent, or Firm*—Finnegan, Henderson, Farabow, Garrett & Dunner

[57] ABSTRACT

A bloodstream velocity image is formed by scanning a two-dimensional region including a blood vessel in a body to be examined with an ultrasonic wave. A velocity profile is formed by distributing either one of average velocities and maximum velocities of bloodstream velocities at a plurality of positions arranged along a first direction, along a second direction which is perpendicular to the first direction and extending across the blood vessel. A bloodstream volume is calculated from the velocity profile and a blood vessel diameter. Thus, an error caused by movement of a blood vessel accompanying pulsation can be decreased.

57 Claims, 8 Drawing Sheets

$V_1$ ; MAX $V_4$ ; MIN $V_6 = (V_2 + V_3 + V_5)/3$

F I G. 9

SMOOTHING

ULTRASONIC DIAGNOSTIC APPARATUS

BACKGROUND OF THE INVENTION

1. Field of the Invention

The present invention relates to an ultrasonic diagnostic apparatus for measuring a bloodstream volume.

2. Description of the Related Art

An instantaneous bloodstream volume (to be merely referred to as a bloodstream volume hereinafter) is obtained by integrating an instantaneous bloodstream velocity for the section of a blood vessel. Since the bloodstream velocity in a blood vessel is not generally uniform (it is fast at the central portion of the blood vessel and slow near the wall of the blood vessel due to the viscosity of the blood), to correctly obtain an instantaneous bloodstream volume, the velocity profile across the axis of the blood vessel must be obtained. In practice, a bloodstream volume is calculated based on a bloodstream velocity of a center of the cross-section of the blood vessel and the cross-section. A method of obtaining the velocity profile along a profile axis of the cross-section of a blood vessel and calculating the instantaneous bloodstream volume based on the velocity profile is usually employed under an assumption that the section of a blood vessel is circular. This calculation of the instantaneous bloodstream volume includes the following various factors that cause errors.

(1) As the blood vessel moves in accordance with the respiration and motion of the heart, the profile axis and the cross-sectional position change relative to each other.

(2) As the range (dynamic range) of detectable minimum and maximum bloodstream velocities is widely set in accordance with the maximum velocity in one heartbeat in order to avoid "aliasing" the velocity resolution at a low velocity is degraded.

(3) A signal level can become zero mainly due to scattering noise, and accordingly the apparent bloodstream velocity becomes zero even when a bloodstream exists.

(4) Since a reverse bloodstream component is added as a negative value, a one-heartbeat ejection volume expressing the total of forward bloodstream components of one heartbeat cycle cannot be obtained.

(5) Although a blood vessel diameter is increased and decreased in accordance with the motion of the heart, the same blood vessel diameter is used in practice throughout all the time phases.

(6) The precision of the one-heartbeat ejection volume is determined by the time and space resolutions. Since the time and space resolutions are inversely proportional to each other, an increase in precision is limited.

(7) No means is available for the observer to confirm whether or not an obtained instantaneous bloodstream volume includes an error.

SUMMARY OF THE INVENTION

The present invention has been made to cope with the above situations, and has as its object to provide an ultrasonic diagnostic apparatus capable of measuring a bloodstream volume at high precision.

According to the present invention an ultrasonic diagnostic apparatus comprising: scanning means for scanning a two-dimensional region including a blood vessel in a body with an ultrasonic wave; bloodstream velocity image forming means for calculating bloodstream velocities at a plurality of positions in the two-dimensional region by using outputs from the scanning means, and forming a bloodstream velocity image; region-of-interest setting means for setting a two-dimensional region of interest in the bloodstream velocity image so as to extend across the blood vessel; velocity profile forming means for forming a velocity profile by distributing either one of average velocities and maximum velocities of the bloodstream velocities arranged along a first direction within the region of interest, along a second direction which is perpendicular to the first direction and extending across the blood vessel; bloodstream volume calculating means for calculating a bloodstream volume from the velocity profile and a diameter of the blood vessel; and display means for displaying the bloodstream volume.

Conventionally, the bloodstream volume is calculated by using only the velocity profile of the bloodstream velocity along the direction (second direction) extending across the blood vessel. Since a blood vessel constantly moves in accordance with the respiration and motion of the heart (pulsation), the positions of the profile axis of the velocity profile and the blood vessel relative to each other are not constant, and their observed positions differ from each other between a bloodstream volume at a certain heartbeat time phase and a bloodstream volume at another heartbeat time phase. The present invention can decrease this problem. According to the present invention, the bloodstream velocities are not merely distributed along the second direction, but the bloodstream velocities are averaged along the first direction perpendicular to the second direction and distributed along the second direction, thereby forming a velocity profile. By this processing, a relative positional error between the velocity profile and the blood vessel which is caused by the movement of the blood vessel in the first direction is substantially decreased.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

DETAILED DESCRIPTION OF THE PREFERRED EMBODIMENT

Figure 1:
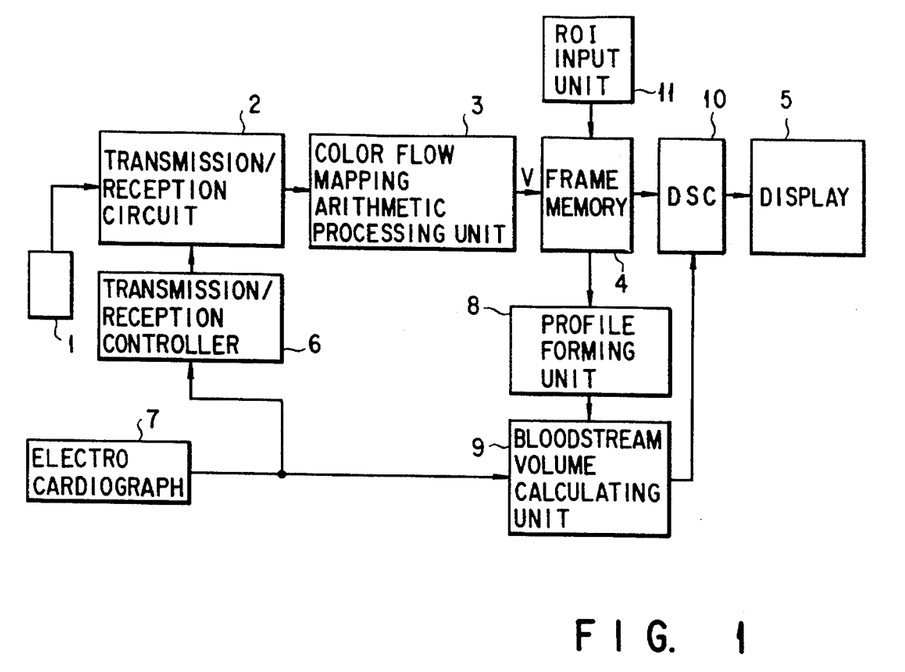
FIG. 1 is a block diagram showing an ultrasonic diagnostic apparatus according to an embodiment of the present invention.

An ultrasonic diagnostic apparatus according to an embodiment of the present invention will be described with reference to the accompanying drawings. FIG. 1 is a block diagram of this embodiment. A plurality of piezoelectric elements are aligned at the distal end of an ultrasonic probe 1. In this embodiment, the ultrasonic probe 1 will be described as an electronic scanning type ultrasonic probe corresponding to sector scanning. However, ultrasonic probes of other scanning schemes, e.g., linear scanning, are not excluded. A transmission/reception circuit 2 scans a two-dimensional region including the blood vessel of a body to be examined through the ultrasonic probe 1 in accordance with the pulse Doppler method. More specifically, the transmission/reception circuit 2 repeatedly transmits an ultrasonic pulse in one direction in accordance with a repetition frequency and sequentially shifts the transmitting/receiving direction of the ultrasonic wave in a predetermined direction while receiving the reflected wave of each transmitted wave, thereby scanning the two-dimensional region.

A color flow mapping arithmetic processing unit 3 calculates the bloodstream velocities at a plurality of positions in the two-dimensional region scanned by the ultrasonic wave. Since this color flow mapping technique is known and does not represent the characteristic feature of the present invention, a detailed description thereof will be omitted. In practice, a position is defined as a range called a sample volume having a certain size due to spreading of the ultrasonic beam and the like. A bloodstream velocity is defined as an average velocity in accordance with the average frequency of the spectra of the reflected waves. The bloodstream velocities calculated by the color flow mapping arithmetic processing unit 3 are sequentially written in a frame memory 4 in accordance with address signals sent from a scan controller (not shown). Thus, a two-dimensional profile (bloodstream velocity image) of the bloodstream velocity is formed. A display 5 displays the bloodstream velocity image supplied from a frame memory 4 through a digital scan converter 10 in color.

The transmission/reception circuit 2 can change the range (dynamic range) of detectable maximum and minimum velocities. Examples of a method of changing the dynamic range are a method of changing the width between the maximum and minimum velocities, a method so-called zero shift in which the maximum and minimum velocities are shifted by the same amount in the same polarity while fixing the width between them to a constant value, and a method obtained by combining these two methods. A bloodstream velocity is determined in accordance with a Doppler shift frequency, and a frequency component exceeding $f0 \pm \frac{1}{2} fr$ is turned in the opposite polarity and cannot be detected. Hence, a dynamic range D is defined as:

$$f0 - \tfrac{1}{2} fr \geq D \geq f0 + \tfrac{1}{2} fr$$

wherein $f0$ is the center frequency of the transmitted ultrasonic waves and $fr$ is the repetition frequency. Due to zero shift, the dynamic range D changes to satisfy:

$$f0 - \tfrac{1}{4} fr \geq D \geq f0 + \tfrac{3}{4} fr$$

As is apparent from the above inequalities, when the repetition frequency $fr$ changes, the width of the dynamic range D is changed accordingly. In other words, the transmission/reception circuit 2 can change the repetition frequency $fr$. The transmission/reception circuit 2 can also change the shift amount. If alternate scanning is employed as the scanning scheme, the repetition frequency $fr$ changes in accordance with the number of alternation cycles.

A bloodstream velocity periodically changes in accordance with pulsation of the heart. Therefore, in order to obtain the maximum velocity in the heartbeat cycle and to sufficiently maintain the velocity resolution at a low velocity, the dynamic range D is preferably changed in accordance with the heartbeat time phase. The present invention realizes this. A transmission/reception controller 6 controls the transmission/reception circuit 2 to change its dynamic range D in accordance with the heartbeat time phase. For this purpose, the transmission/reception controller 6 retains an optimum dynamic range D for each of the plurality of heartbeat time phases and supplies a repetition frequency $fr$ and/or a shift amount, and (the data of) the number of alternation cycles depending on the case, which are necessary for realizing each dynamic range D, to the transmission/reception circuit 2 in accordance with the heartbeat time phase of the body to be examined.

Furthermore, the transmission/reception controller 6 outputs a trigger to the transmission/reception circuit 2. The transmission/reception circuit 2 starts two-dimensional scanning upon reception of this trigger. The transmission/reception controller 6 slightly changes the heartbeat time phases at which it outputs the trigger among continuous heartbeat cycles. Thus, the transmission/reception circuit 2 can scan the two-dimensional region at timings of the different heartbeat time phase by setting a plurality of cycles, e.g., three cycles, as one period.

An electrocardiograph 7 detects the heartbeat time phase of the body to be examined on the time base. An electrocardiogram is obtained as series of P, Q, R, S, T, and U waves. In this embodiment, a time having elapsed from the most characteristic R wave is defined as the heartbeat time phase. The transmission/reception controller 6 recognizes the heartbeat time phase of the body to be examined from the output from the electrocardiograph 7.

An ROI input unit 11 is an input equipment, e.g., a mouse, which is operated by the operator. A region of interest (ROI) for determining the range of measurement of the instantaneous bloodstream volume (to be referred to merely as the "bloodstream volume" hereinafter) is set on the bloodstream velocity image through the ROI input unit 11 to extend across the blood vessel. A plurality of positions are always two-dimensionally included in the ROI. A direction along the blood vessel is called the first direction, and a direction across the blood vessel and obtained a velocity profile is called the second direction. The first and second directions will be employed as required.

Data (bloodstream velocities) of a plurality of pixels included in the ROI set through the ROI input unit 11 are loaded from the frame memory 4 into a profile forming unit 8.

The profile forming unit 8 calculates the average velocities by averaging the bloodstream velocities at the plurality of positions in the ROI along the first direction, and distributes average velocities whose positions along the second direction are different, thereby forming a velocity profile along the second direction that is across the blood vessel. The profile forming unit 8 can form the velocity profile by using the maximum velocities of the bloodstream velocities at the plurality of positions in the ROI that are adjacent to each other along the first direction in place of the average velocities described above.

This velocity profile is supplied to a bloodstream volume calculating unit 9. The instantaneous bloodstream volume calculating unit 9 calculates the instantaneous bloodstream volume based on the velocity profile and the blood vessel diameter. The bloodstream volume calculating unit 9 also calculates the unit time bloodstream volume per a unit time (ex. one minute) based on the bloodstream volume. The bloodstream volume calculating unit 9 also calculates an average unit time bloodstream volume by averaging unit time bloodstream volumes obtained in succession. The bloodstream volume calculating unit 9 also calculates a stroke volume by adding the instantaneous bloodstream volumes of different heartbeat time phases within one heartbeat cycle. The bloodstream volume calculating unit 9 also calculates an average stroke volume by averaging the stroke volumes which are obtained in succession. The unit 9 also calculates a cardiac output volume by multiplying a stroke volume with a heart rate. The unit 9 also calculates an average cardiac output volume by averaging cardiac output volumes obtained in succession.

The respective bloodstream volumes calculated by the bloodstream volume calculating unit 9 are displayed on the display 5 through the digital scan converter 10.

Figure 2:
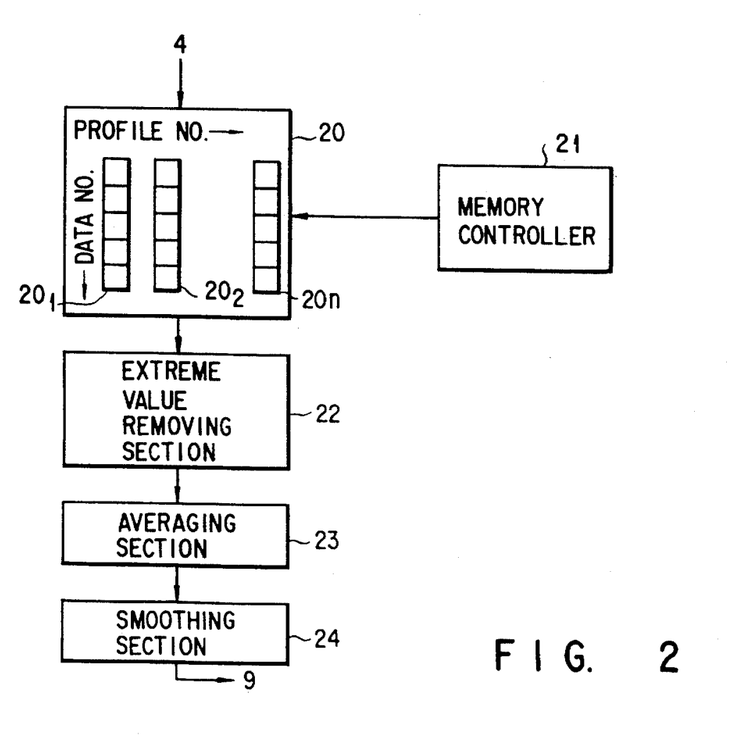
FIG. 2 is a block diagram of a profile forming unit of FIG. 1.

FIG. 2 is a block diagram of the profile forming unit 8. The bloodstream velocity data in the ROI read from the frame memory 4 is temporarily held in a memory 20. The memory 20 has registers $20_1$ to $20_n$. The bloodstream velocity data at the positions aligned along the second direction are controlled by a memory controller 21 such that these data are sequentially fetched by the same register. Assume that the number of positions along the second direction, i.e., the data count is N. A velocity profile expressed by the plurality of bloodstream velocity data at the positions fetched by each register corresponds to the conventional velocity profile. That is, the memory 20 holds n different velocity profiles that are spatially parallel to each other.

Bloodstream velocity data having the same data number are read from each of the registers $20_1$ to $20_n$ into an extreme value removing section 22 by the control operation of the memory controller 21. The extreme value removing section 22 removes the maximum and minimum velocities from the bloodstream velocity data having the same data number and supplies the remaining bloodstream velocity data to an averaging section 23. The averaging section 23 calculates each average velocity by averaging the remaining bloodstream velocities. Note that this average velocity is an average of the bloodstream velocities and is different from the average velocity in accordance with the average frequency of the spectrum of the reflected wave described in the beginning of the Detailed Description of the Preferred Embodiment, i.e., it is different from the bloodstream velocity defined there. The averaging section 23 repeats averaging operations for all the data numbers. The velocity profile obtained by distributing the average velocities of the respective data numbers by plotting the velocity along the axis of ordinate and the data number along the axis of abscissa is smoothed by a smoothing section 24, so that signal omissions caused by scattering noise, i.e., so-called black omissions, are compensated for. For the smoothing operation, any of various conventional schemes may be employed. For example, if the maximum value hold scheme is employed, the processing operation of replacing the maximum velocity of the bloodstream velocities of each of a plurality of, e.g., five, close data numbers by the data of the central data number is repeated along the axis of abscissa. Finally, the smoothed velocity profile is sent to the bloodstream volume calculating unit 9.

Figure 3:
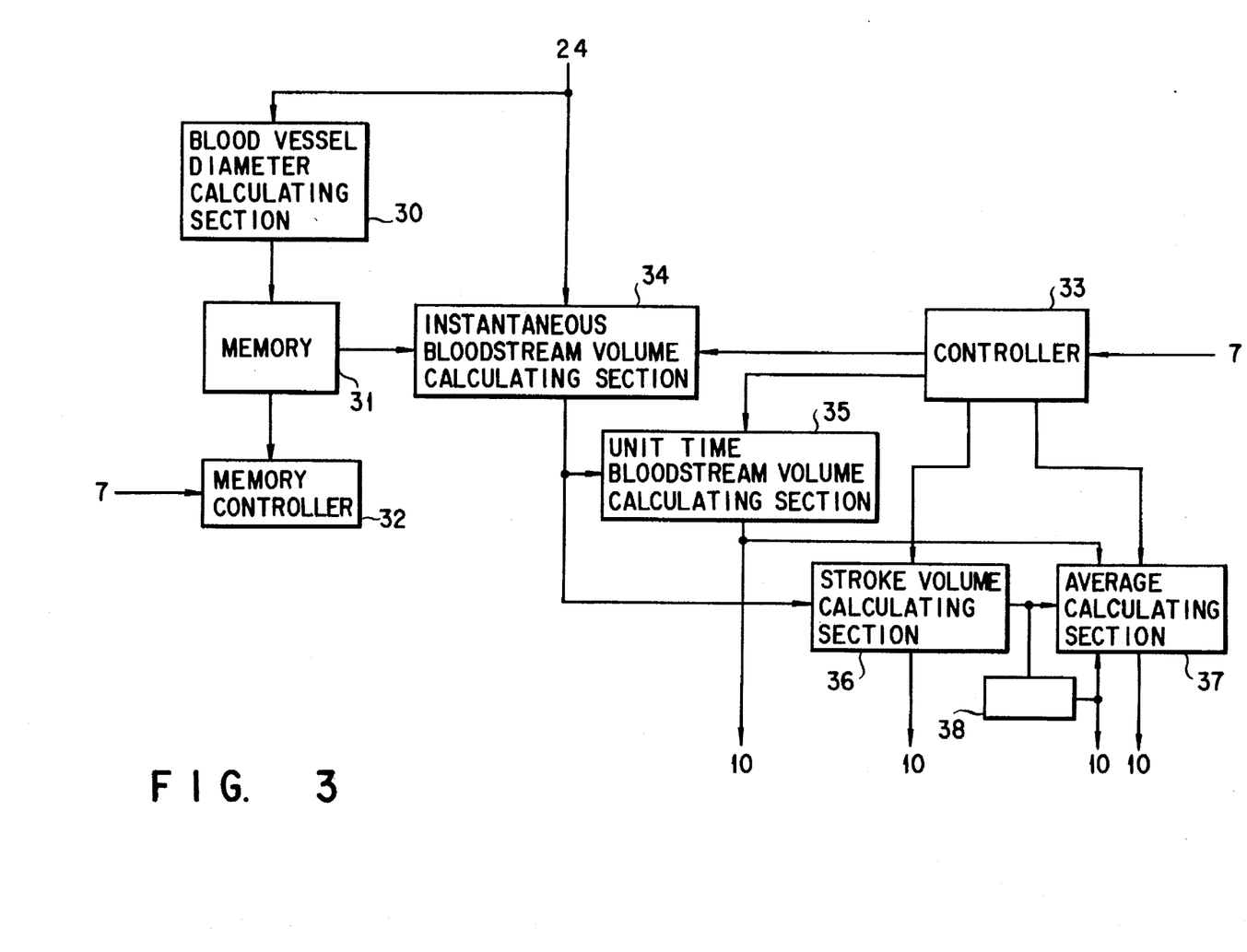
FIG. 3 is a block diagram of a bloodstream volume calculating unit of FIG. 1.

FIG. 3 is a block diagram of the bloodstream volume calculating unit 9. The velocity profile formed by the ROI input unit 11 is sent to an instantaneous bloodstream volume calculating section 34 and a blood vessel diameter calculating section 30. The blood vessel diameter calculating section 30 calculates the blood vessel diameter based on the velocity profile. The calculated blood vessel diameter is written in a memory 31 by the control operation of a memory controller 32 to correspond to the heartbeat time phase of the body to be examined obtained during scanning. The blood vessel diameter is calculated at each of the plurality of different heartbeat time phases in one heartbeat cycle, and is written in the memory 31 to correspond to the heartbeat time phase of the body to be examined which is obtained during scanning. When a bloodstream volume is to be calculated, a blood vessel diameter according to the heartbeat time phase of the body to be examined is supplied to the instantaneous bloodstream volume calculating section 34 by the control operation of the memory controller 32.

The instantaneous bloodstream volume calculating section 34 calculates the bloodstream volume (instantaneous bloodstream volume) based on the velocity profile formed by the profile forming unit 8 and the blood vessel diameter sent from the memory 31. This bloodstream volume is sent to a unit time bloodstream volume calculating section 35 and a stroke volume calculating section 36. The unit time bloodstream volume calculating section 35 converts the instantaneous bloodstream volume to the unit time bloodstream volume. This unit time bloodstream volume is sent to the digital scan converter 10 and an average calculating section 37. The stroke volume calculating section 36 calculates the stroke bloodstream volume ejected while the heart pulsates once, by adding the instantaneous bloodstream volumes at different heartbeat time phases within one heartbeat cycle. Especially, the stroke volume calculating section 36 excludes the instantaneous bloodstream volumes having a negative polarity (reverse bloodstreams) from the addition target and adds only the bloodstream volumes having a positive polarity (forward bloodstreams), thereby accurately calculating a stroke volume. Furthermore, since the transmission/reception circuit 2 sets a plurality of continuous cycles, e.g., three cycles, as one period and scans the two-dimensional region at timings of different heartbeat time phases in this period by the operation of the transmission/reception controller 6, the stroke volume calculating section 36 can calculate a stroke volume having a high precision by adding the bloodstream volumes of one heartbeat cycle. The stroke volume is sent to the digital scan converter 10, a cardiac output volume calculating section 38 and an average calculating section 37. The cardiac output volume calculating section 38 calculates a cardiac output volume by multiplying the stroke volume with a heart rate. The cardiac output volume is sent; the digital scan converter 10 and the average calculating section 37. The average calculating section 37 calculates an average unit time bloodstream volume, an average stroke volume, and an average cardiac output volume. These average volumes are sent to the digital scan converter 10.

The operation of this embodiment having the above arrangement will be described.

Figure 4:
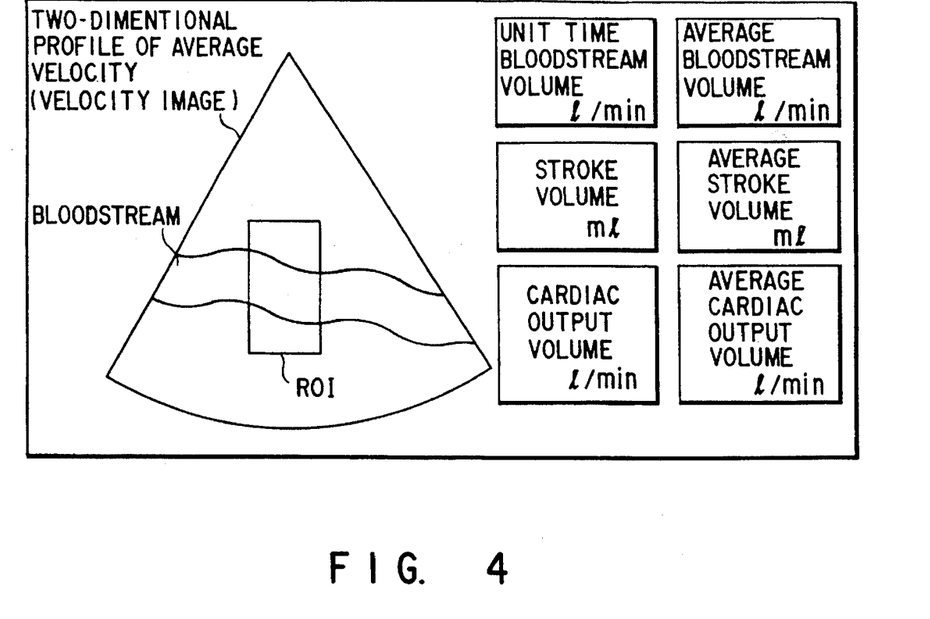
FIG. 4 shows a display screen.
Figure 5A:
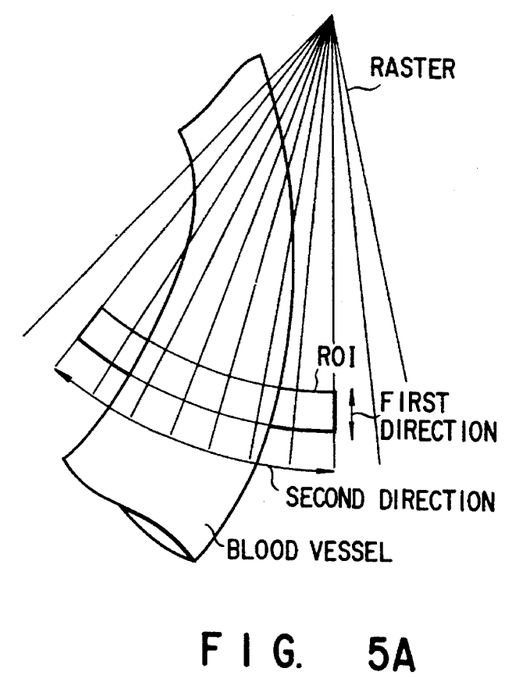
FIGS. 5A to 5C show preset patterns of an ROI.
Figure 5B:
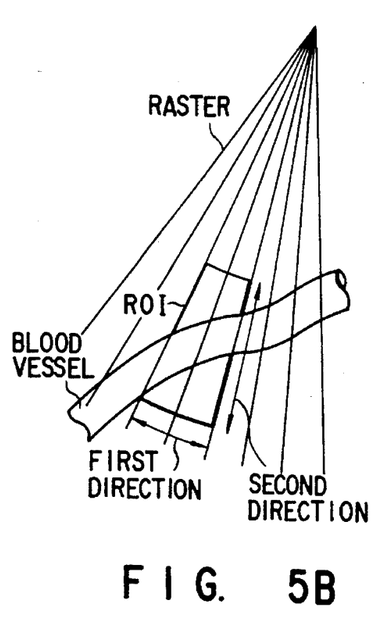
Figure 5C:
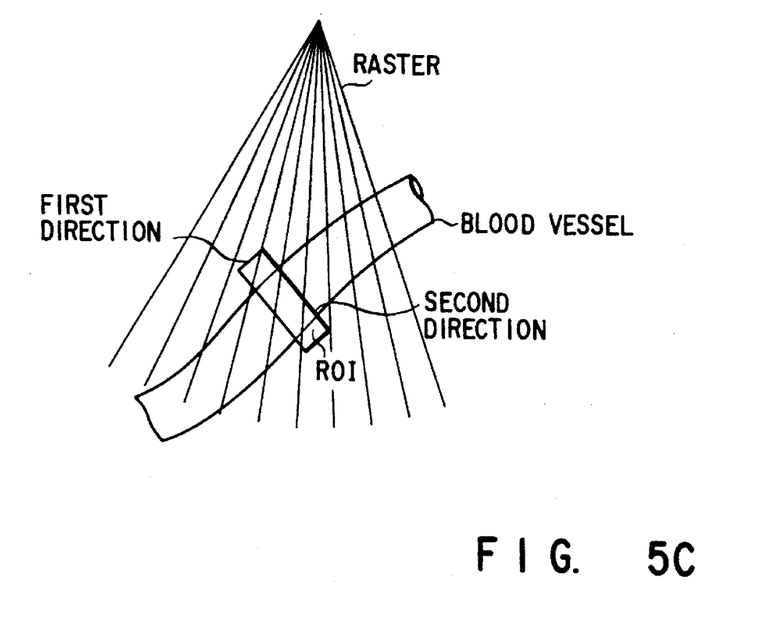

FIG. 4 shows the display screen of the display 5. First, an ROI, the bloodstream volume of which is to be measured, is set on the bloodstream velocity image through the ROI input unit 11 to extend across the blood vessel. The ROI is preferably set by 4-point designation or diagonal 2-point designation from the viewpoint of easy setting. FIGS. 5A, 5B, and 5C show the method of setting the ROI of cases in which the travel directions of the blood vessel are different. FIG. 5A shows an ROI which is set to be perpendicular to the raster; FIG. 5B shows an ROI which is set along the raster; and FIG. 5C shows an ROI which is set to be perpendicular to the blood vessel regardless of the raster. The ROI is set by either method in accordance with the travel direction of the blood vessel. In FIG. 5A, the axis of abscissa of the velocity profile is drawn perpendicularly to the raster. In FIG. 5B, the axis of abscissa of the velocity profile is drawn along the raster. The schemes of calculating the bloodstream volume slightly differ among FIGS. 5A, 5B, and 5C. Since these calculating schemes are known and do not represent the characteristic feature of the present invention, a detailed description thereof will be omitted and be described by way of the case of FIG. 5B.

Figure 6A:
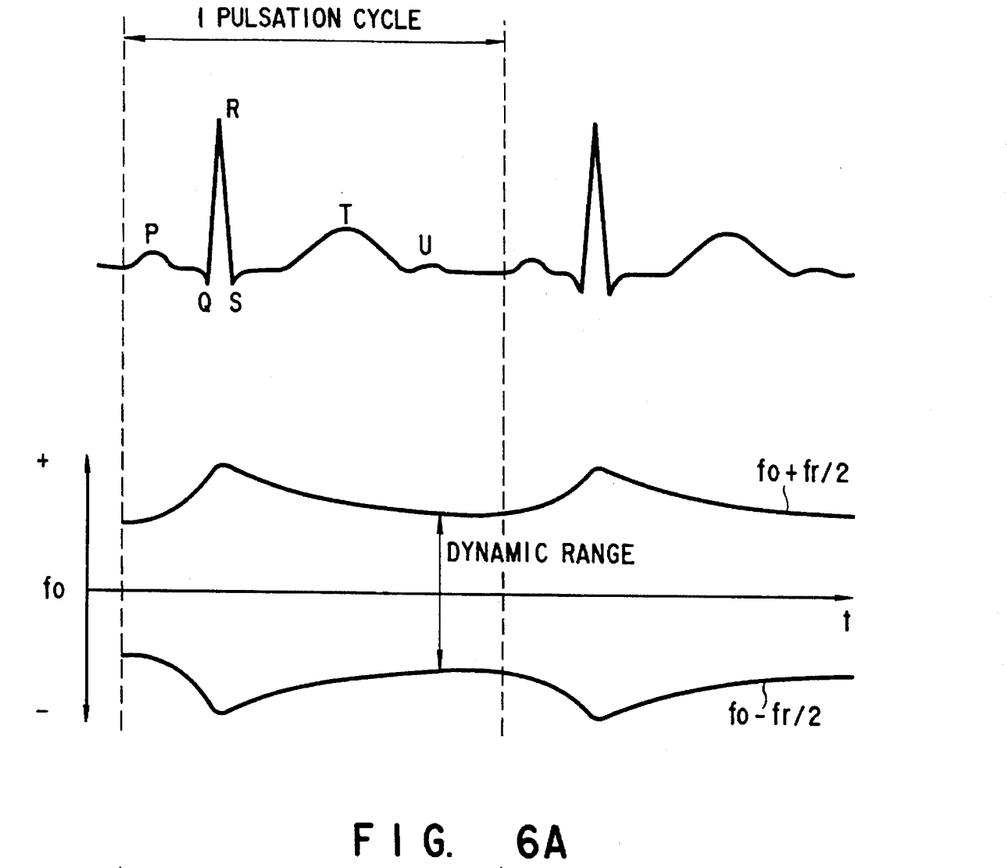
FIGS. 6A and 6B are graphs showing a change over time in dynamic range caused by the control operation of a transmission/reception controller of FIG. 1.
Figure 6B:
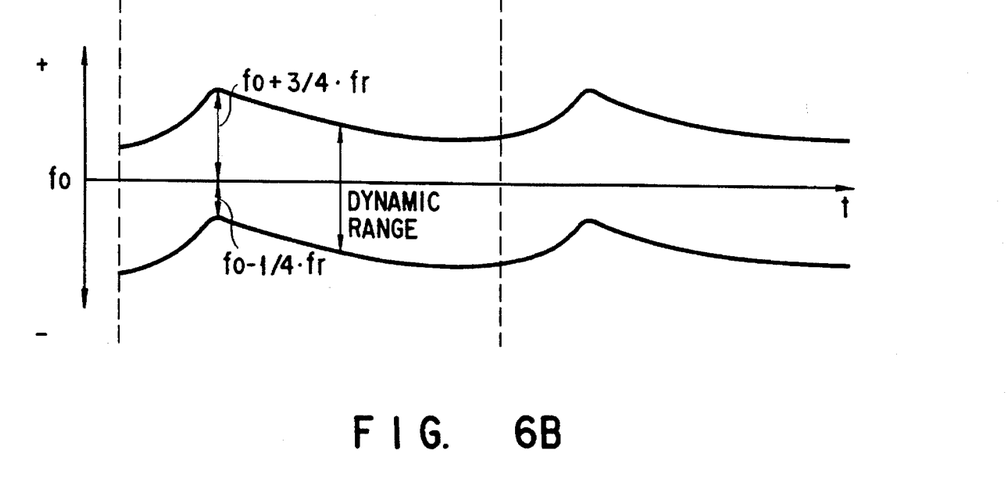

When the ROI is set, the two-dimensional region of the body to be examined is repeatedly scanned with the ultrasonic wave. As described above, the dynamic range D of the transmission/reception circuit 2 is changed by the control operation of the transmission/reception controller 6 in accordance with the heartbeat time phase of the body to be examined which is detected by the electrocardiograph 7. The dynamic range D is changed by changing the repetition frequency fr and/or the shift amount by the transmission/reception circuit 2. FIG. 6A shows a change over time in dynamic range D wherein the repetition frequency fr is changed. FIG. 6B shows a change over time in dynamic range D wherein the dynamic range D is shifted to the positive side by ¼.fr. Although the bloodstream velocity is periodically changed by pulsation of the heart, the maximum velocity in the heartbeat cycle can be obtained, and the velocity resolution at a low speed can be sufficiently maintained.

Figure 7:
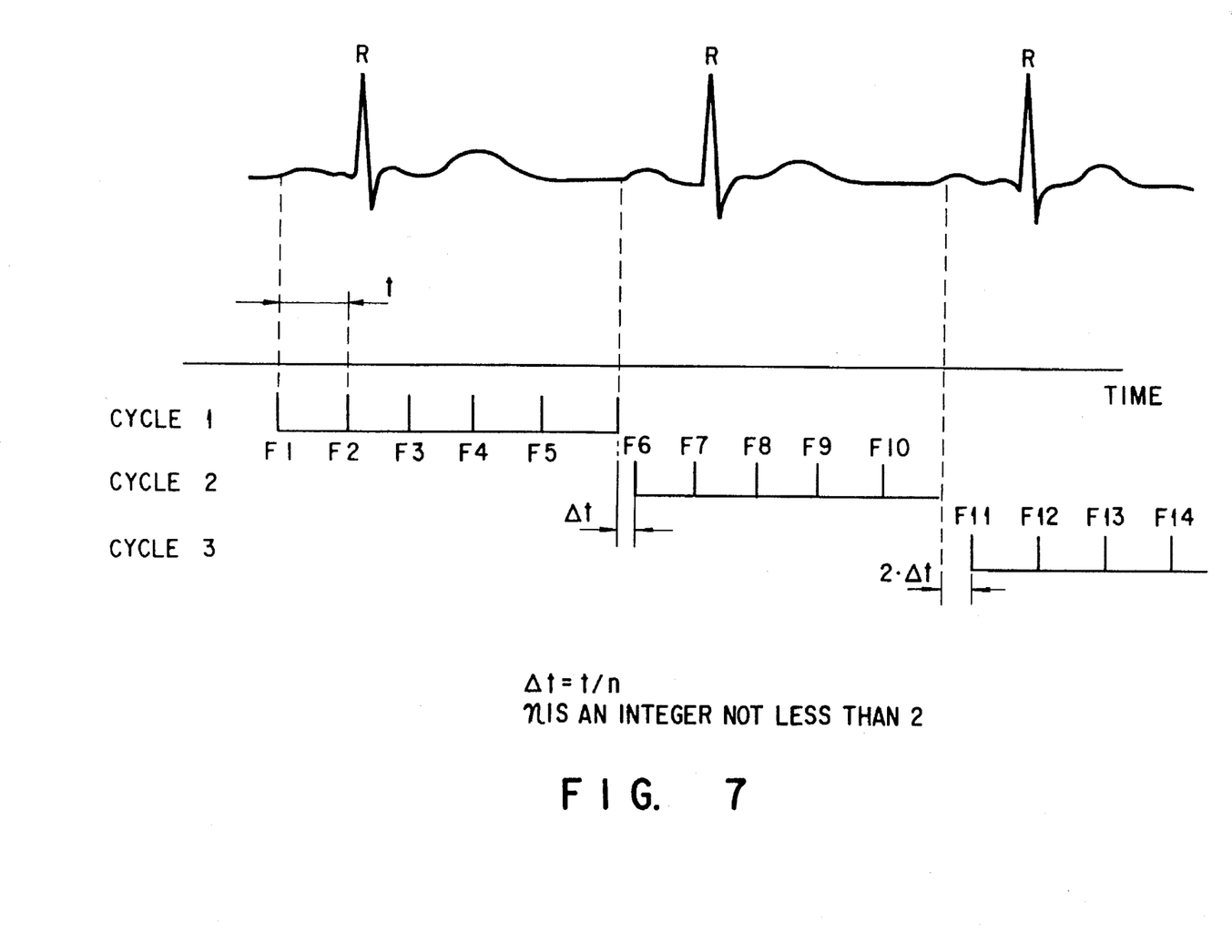
FIG. 7 is a graph for explaining a difference in timing of two-dimensional scanning among cycles.

The transmission/reception controller 6 slightly shifts the heartbeat time phase at which it outputs a trigger to the transmission/reception circuit 2 among continuous heartbeat cycles. FIG. 7 shows the relationship in time between the scanning timing (output timing of the trigger) and the heartbeat time phase in a case wherein three cycles constitute one period. Referring to FIG. 7, reference symbol F denotes the scanning timing; t, the repetition frequency of two-dimensional scanning; and $\Delta t$, a shift in time among cycles. The timing t and $\Delta t$ are set to satisfy the following equation:

$$\Delta t = t/n$$

where n is an integer of 2 or more and the number of cycles constituting one period. In this example, n is set to 3. When the scanning timing is set to have a time shift $\Delta t$ among cycles in this manner, all the scanning timings of one period correspond to different heartbeat time phases, and a bloodstream volume having a high precision can be obtained. Thus, a high-precision stroke volume can be calculated from the bloodstream volumes obtained within one period.

Figure 8:
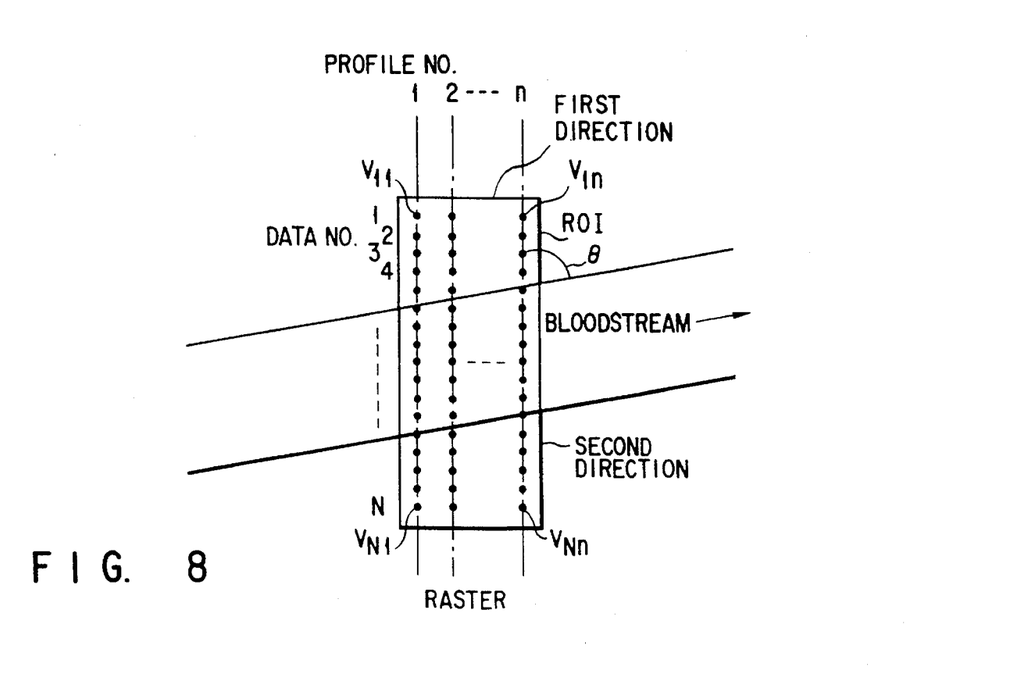
FIG. 8 is a diagram showing the arrangement of positions in the ROI.
Figure 9:
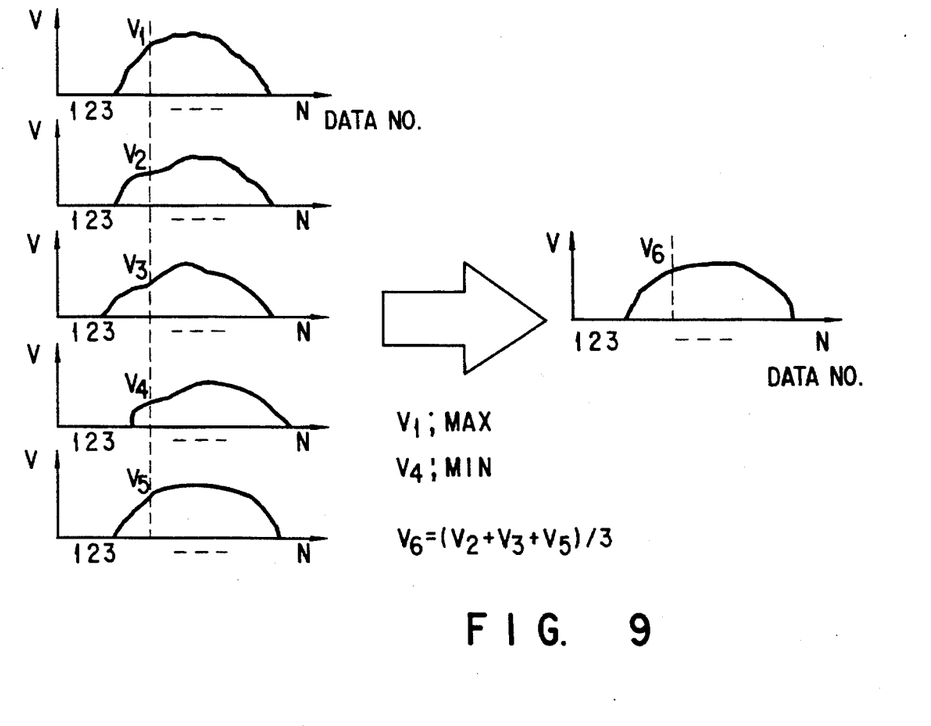
FIG. 9 includes graphs for explaining the method of forming a profile by a profile forming unit of FIG. 1.

A method of forming the velocity profile will be described. FIG. 8 shows the arrangement of the positions in the ROI. The horizontal direction on the surface of the sheet of FIG. 8 corresponds to the first direction, and the vertical direction thereof corresponds to the second direction. The bloodstream velocities of the respective positions are described as $V_{11}, V_{1n}, \ldots$ to $V_{Nn}$. FIG. 9 includes graphs for explaining the method of forming the velocity profile by the ROI input unit 11. In FIG. 9, n 32 5.

Bloodstream velocities $V_{11}, V_{1n} \ldots$, and $V_{Nn}$ in the ROI are sent from the frame memory 4 to the memory 20 of the profile forming unit 8, and bloodstream velocity data having the same file numbers are stored in the same corresponding registers $20_1$ to $20_n$. Each of the velocity profiles expressed by the bloodstream velocity data fetched by the respective registers $20_1$ to $20_n$ corresponds to the conventional velocity profile. That is, the memory 20 holds 5 velocity profiles that are spatially parallel to each other and extend along the profile axis. Bloodstream velocity data having the same data number are read from each of the registers $20_1$ to $20_n$ into the extreme value removing section 22 by the control operation of the memory controller 21. Maximum and minimum velocities Vmax and Vmin are removed from the bloodstream velocity data having the same data number by the extreme value removing section 22, and the remaining bloodstream velocity data are supplied to the averaging section 23. The remaining bloodstream velocities are averaged by the averaging section 23, thereby calculating the average velocity. Note that this average velocity is the average of the bloodstream velocities and is different from the average velocity in accordance with the average frequency of the spectrum of the reflected wave described in the beginning of the Detailed Description of the Preferred Embodiment, i.e., it is different from the bloodstream velocity defined there. The averaging operations are repeated for all the data numbers by the averaging section 23, and a plurality of different average velocities having different data numbers, in other words, a plurality of different average velocities of different positions along the second direction are obtained. These plurality of different average velocities are distributed in accordance with the data numbers, thereby forming a velocity profile. The velocity profile is formed not by distributing the bloodstream velocities along the second direction but by distributing the average velocities, obtained by spatially averaging the bloodstream velocities along the first direction, along the second direction across the blood vessel. Therefore, positional errors along the first direction with respect to the blood vessel, which are caused due to the movement of the blood vessel along the first direction, are substantially decreased.

As described above, the profile forming unit 8 can form the velocity profile by using the maximum velocities of the bloodstream velocities at the positions in the ROI that are adjacent to each other along the first direction in place of the average velocities described above. In this case, the same effect as that obtained when the average velocities are used can be obtained.

Figure 10:
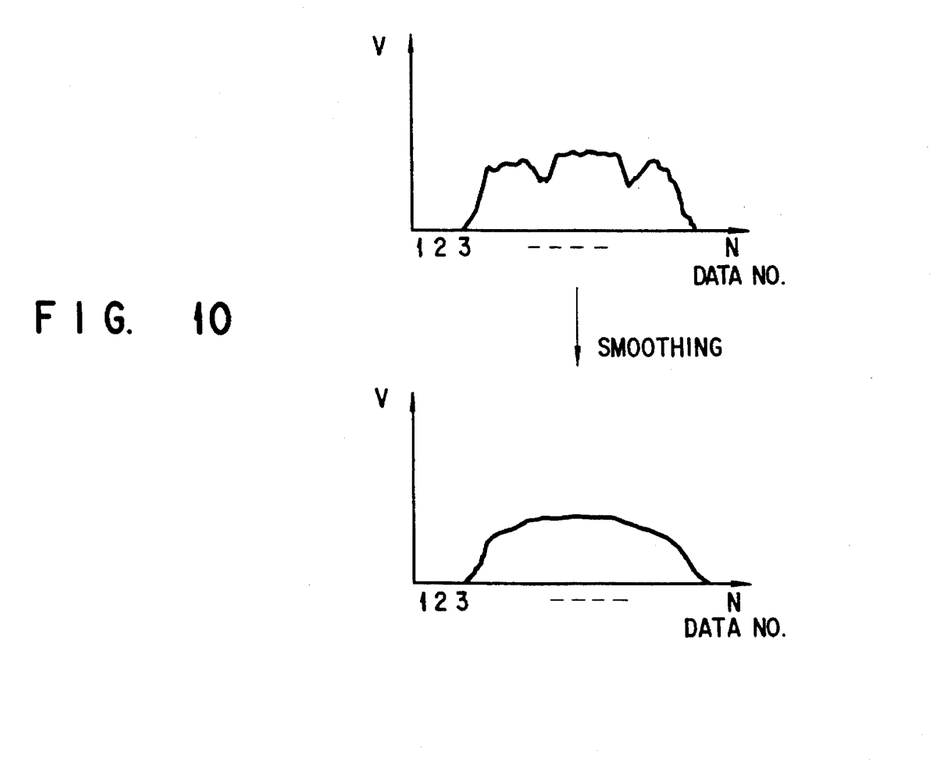
FIG. 10 includes graphs showing smoothing performed by a smoothing section of FIG. 2.

As shown in FIG. 10, this velocity profile is smoothed by the smoothing section 24 to compensate for signal omissions caused by scattering noise, i.e., caused by so-called black omissions (kuro-nuke). The smoothed velocity profile is sent to the bloodstream volume calculating unit 9.

Figure 11:
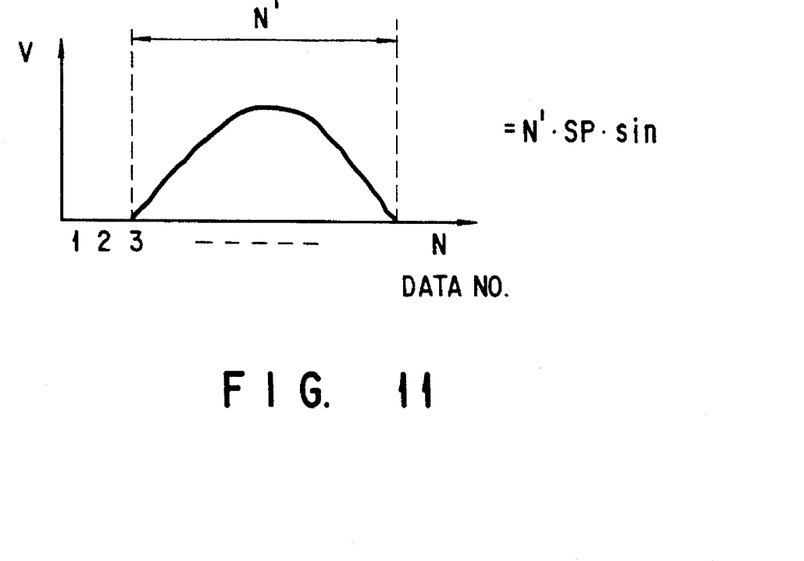
FIG. 11 is a graph for explaining a method of calculating a blood vessel diameter by a blood vessel diameter calculating section of FIG. 3.
Figure 12:
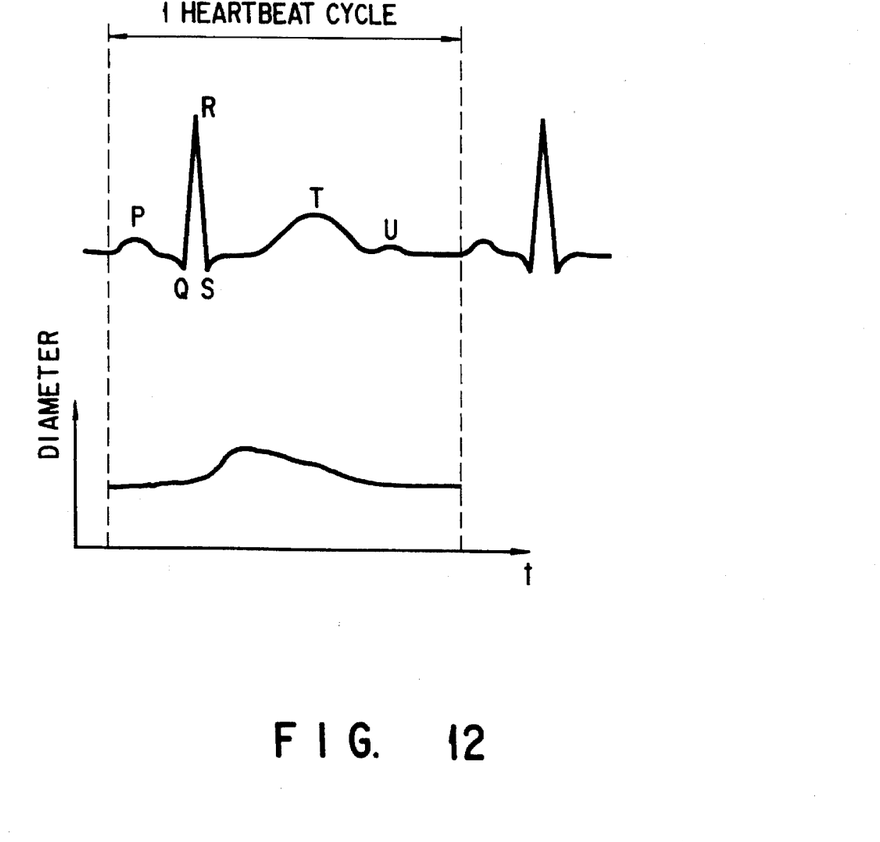
FIG. 12 is a graph showing a change in blood vessel diameter in accordance with a change in heartbeat time phase.

FIG. 11 is a graph for explaining the method of calculating the blood vessel diameter and showing the velocity profile. The blood vessel diameter is calculated by the blood vessel diameter calculating section 30 of the bloodstream volume calculating unit 9 based on the velocity profile. A bloodstream does not exist outside the blood vessel, as a matter of course. Accordingly, the blood vessel diameter is determined in accordance with the range from the rise to the fall of the velocity profile, i.e., in accordance with the range exceeding velocity of 0 (in practice, a threshold VTH exceeding 0 is set by considering the influence of noise). A number N' of data included in this range is multiplied with the distance in accordance with the position pitch, i.e., the sampling pitch on the same raster in this case, and the product is corrected by the angle defined by the bloodstream and the raster, thereby calculating the blood vessel diameter. The calculated blood vessel diameter is written in the memory 31 by the control operation of the memory controller 32 to correspond to the heartbeat time phase of the body to be examined during this scanning. The instantaneous bloodstream volume calculating section 34 calculates the instantaneous bloodstream volume based on this blood vessel diameter and the velocity profile corresponding to the heartbeat time phase. Thus, an error in bloodstream volume caused by a change in blood vessel diameter accompanying pulsation of the heart can be eliminated. The blood vessel diameter may be obtained based on ∫an M mode image". Similarly, as two-dimensional scanning is repeatedly performed, the blood vessel diameter and the instantaneous bloodstream volume are calculated for each of the plurality of different heartbeat time phases within one heartbeat cycle, and is written in the memory 31 to correspond to the heartbeat time phase of the body to be examined during each scanning. FIG. 12 shows a change in blood vessel diameter in accordance with a change in heartbeat time phase.

The blood vessel diameters of all the heartbeat time phases in the heartbeat cycle are calculated before calculating the bloodstream volume in this manner and stored in the memory 31, and the blood vessel diameter of the corresponding heartbeat time phase may be supplied to the instantaneous bloodstream volume calculating section 34 in calculating the bloodstream volume.

The scheme of calculating the bloodstream volume will be briefly explained. A bloodstream volume can be calculated in accordance with the following equation:

$$\sum_{i=1}^{N} \delta i \cdot \pi \cdot r^2 \cdot Vi/\cos\theta$$

where θ is the angle defined by the bloodstream and the raster, r is the blood vessel diameter, and δi is the coefficient for converting the sectional area into an annular area. This instantaneous bloodstream volume is sent to the unit time bloodstream volume calculating section 35 and the stroke volume calculating section 36. The unit time bloodstream volume calculating section 35 converts the instantaneous bloodstream volume to the unit time bloodstream volume. The average calculating section 37 averages unit time bloodstream volumes to obtain the average unit time bloodstream volume. The average unit time bloodstream volume is displayed simultaneously with the unit time bloodstream volume as shown in FIG. 4 through the digital scan converter 10. The observer can observe the unit time bloodstream volume and the average unit time bloodstream volume simultaneously, and estimate the presence/absence and the degree of an error component in the calculated bloodstream volume by referring to the difference between them.

The stroke volume calculating section 36 adds the instantaneous bloodstream volumes at different heartbeat time phases obtained within one period to obtain a stroke volume. Since the stroke volume calculating section 36 excludes the instantaneous bloodstream volumes having a negative polarity (reverse bloodstream) from the addition target and adds only the instantaneous bloodstream volumes having a positive polarity (forward bloodstream), it calculates the true stroke volume. Furthermore, since the transmission/reception circuit 2 sets a plurality of continuous heartbeat cycles, e.g., 3 heartbeat cycles, as one period by the transmission/reception controller 6 and scans the two-dimensional region at timings of different heartbeat time phases, it can calculate a stroke volume having a high precision by adding the instantaneous bloodstream volumes of one period. The stroke volume is sent to the average calculating section 37, the cardiac volume calculating section 38 and the digital scan converter 10. The average calculating section 37 calculates the average stroke volume by averaging the stroke volumes that are continuously obtained. The average stroke volume is sent to the digital scan converter 10 and displayed simultaneously with the stroke volume. The observer can observe the stroke volume and the average stroke volume simultaneously, and estimate the presence/absence and the degree of an error component in the obtained stroke volume by referring to the difference between them.

The cardiac volume calculating section 38 multiplies a stroke volume with a heart rate to obtain a cardiac volume. The cardiac volume is sent the average calculating section 37 and the digital scan converter 10. The average calculating section 37 averages cardiac volumes that are continuously obtained to obtain an average cardiac volume. The average cardiac volume is sent to the digital scan converter 10, and is displayed simultaneously with the cardiac volume. The observer can observe the cardiac volume and the average cardiac volume simultaneously, and estimate the presence/absence and the degree of an error component in the obtained cardiac volume by referring to the difference between them.

In this manner, according to this embodiment, the bloodstream volume can be measured at high precision by excluding various error factors. The error factors are apparently the movement of the blood vessel in accordance with heartbeat, signal omissions due to black omissions, an inappropriate dynamic range for the actual bloodstream velocity, and a change in blood vessel diameter in accordance with heartbeat. Since the unit time bloodstream volume, the stroke volume and the cardiac volume are displayed simultaneously with their averages, whether or not errors are included in each volume can be determined. Furthermore, since the timings of two-dimensional scanning are changed among heartbeat cycles, the precision of the stroke volume is substantially increased.

It is apparent that the present invention is not limited to the above embodiment, and various changes and modifications may be made within the spirit and scope of the invention. For example, each of the unit time bloodstream volume, the average unit time bloodstream volume, the stroke volume, the average stroke volume, the cardiac volume and the average cardiac volume may be selected to display.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An ultrasonic diagnostic apparatus comprising:

scanning means for scanning a two-dimensional region including a blood vessel in a body with an ultrasonic wave;

bloodstream velocity image forming means for calculating bloodstream velocities at a plurality of positions in the two-dimensional region by using outputs from said scanning means, and region-of-interest setting means for setting a two-dimensional region of interest in the bloodstream velocity image so as to extend across the blood vessel;

velocity profile forming means for forming a velocity profile by distributing either one of average velocities and maximum velocities of the bloodstream velocities arranged along a first direction within the region of interest, along a second direction which is perpendicular to the first direction and extending across the blood vessel said velocity profile forming means excluding the maximum velocities and minimum velocities of the bloodstream velocities along the first direction from a target averaging performed for calculating the average velocities;

bloodstream volume calculating means for calculating a bloodstream volume from said velocity profile and a diameter of the blood vessel; and display means for displaying the bloodstream volume.

2. An apparatus according to claim 1, further comprising means for controlling said scanning means so as to change a range of detectable maximum and minimum velocities of a bloodstream.

3. An apparatus according to claim 2, in which said control means changes the range of said scanning means in accordance with a heartbeat time phase of the body to be examined.

4. An apparatus according to claim 1, in which said velocity profile forming means includes means for smoothing the velocity profile.

5. An apparatus according to claim 1, further comprising blood vessel diameter calculating means for calculating a blood vessel diameter based on a distance between a rise and a fall of the velocity profile, and supplying the blood vessel diameter to said bloodstream volume calculating means.

6. An apparatus according to claim 5, in which said blood vessel diameter calculating means calculates blood vessel diameters at different heartbeat time phases in one heartbeat cycle, holds calculated blood vessel diameters, and supplies a blood vessel diameter corresponding to the heartbeat time phase of the body to be examined to said bloodstream volume calculating means.

7. An apparatus according to claim 1, in which said bloodstream volume calculating means calculates an average bloodstream volume by averaging bloodstream volumes continuously obtained.

8. An apparatus according to claim 7, in which said display means displays the average bloodstream volume and the bloodstream volume simultaneously.

9. An apparatus according to claim 1, in which said bloodstream volume calculating means calculates a stroke volume by adding bloodstream volumes obtained at different heartbeat time phases in one heartbeat cycle.

10. An apparatus according to claim 9, in which said bloodstream volume calculating means excludes a bloodstream volume having a negative polarity from an addition target for calculating the stroke volume.

11. An apparatus according to claim 9, in which said bloodstream volume calculating means calculates an average stroke volume by averaging stroke volumes which are repeatedly calculated over a plurality of heartbeat cycles.

12. An apparatus according to claim 11, in which said display means displays the stroke volume and the average stroke volume simultaneously.

13. An apparatus according to claim 1, in which said scanning means scans the two-dimensional region by shifting a timing in units of heartbeat cycles, and said bloodstream volume calculating means calculates a stroke volume by adding bloodstream volumes obtained at different heartbeat time phases that are continuously calculated over a plurality of heartbeat cycles.

14. An apparatus according to claim 13, in which said bloodstream volume calculating means excludes a bloodstream volume having a negative polarity from an addition target for calculating the stroke volume.

15. An apparatus according to claim 13, in which said bloodstream volume calculating means calculates an average stroke volume by averaging stroke volumes which are repeatedly calculated over a plurality of heartbeat cycles.

16. An apparatus according to claim 15, in which said display means displays the stroke volume and the average stroke volume simultaneously.

17. An ultrasonic diagnostic apparatus comprising:

scanning means for scanning a two-dimensional region including a blood vessel in a body with an ultrasonic wave;

bloodstream velocity calculating means for calculating bloodstream velocities at a plurality of positions in the two-dimensional region by using outputs from said scanning means;

velocity profile forming means for forming a velocity profile by distributing the bloodstream velocities along a direction extending across the blood vessel;

smoothing means for smoothing the velocity profile;

bloodstream volume calculating means for calculating a bloodstream volume from the velocity profile smoothed by said smoothing means and a diameter of the blood vessel; and display means for displaying the bloodstream volume.

18. An apparatus according to claim 17, further comprising means for controlling said scanning means so as to change a range of detectable maximum and minimum velocities of a bloodstream.

19. An apparatus according to claim 18, in which said control means changes the range of said scanning means in accordance with a heartbeat time phase of the body to be examined.

20. An apparatus according to claim 17, further comprising blood vessel diameter calculating means for calculating a distance between a rise and a fall of the velocity profile as the diameter of the blood vessel and supplying the diameter to said bloodstream volume calculating means.

21. An apparatus according to claim 20, in which said blood vessel diameter calculating means calculates blood vessel diameters at different heartbeat time phases in one heartbeat cycle, holds calculated blood vessel diameters, and supplies a blood vessel diameter corresponding to the heartbeat time phase of the body to be examined to said bloodstream volume calculating means.

22. An apparatus according to claim 17, in which said bloodstream volume calculating means calculates an average bloodstream volume by averaging bloodstream volumes continuously obtained.

23. An apparatus according to claim 22, in which said display means displays the average bloodstream volume and the bloodstream volume simultaneously.

24. An apparatus according to claim 17, in which said bloodstream volume calculating means calculates a stroke volume by adding bloodstream volumes obtained at different heartbeat time phases in one heartbeat cycle.

25. An apparatus according to claim 24, in which said bloodstream volume calculating means excludes a bloodstream volume having a negative polarity from an addition target for calculating the stroke volume.

26. An apparatus according to claim 24, in which said bloodstream volume calculating means calculates an average stroke volume by averaging stroke volumes which are repeatedly calculated over a plurality of heartbeat cycles.

27. An apparatus according to claim 26, in which said display means displays the stroke volume and the average stroke volume simultaneously.

28. An apparatus according to claim 17, in which said scanning means scans the two-dimensional region by shifting a timing in units of heartbeat cycles, and said bloodstream volume calculating means calculates a stroke volume by adding bloodstream volumes obtained at different heartbeat time phases that are repeatedly calculated over a plurality of heartbeat cycles.

29. An apparatus according to claim 28, in which said bloodstream volume calculating means excludes a bloodstream volume having a negative polarity from an addition target for calculating the stroke volume.

30. An apparatus according to claim 28, in which said bloodstream volume calculating means calculates an average stroke volume by averaging stroke volumes which are repeatedly calculated over a plurality of heartbeat cycles.

31. An apparatus according to claim 30, in which said display means displays the stroke volume and the average stroke volume simultaneously.

32. An ultrasonic diagnostic apparatus comprising:

scanning means for scanning a two-dimensional region including a blood vessel in a body with an ultrasonic wave;

bloodstream velocity calculating means for calculating bloodstream velocities at a plurality of positions in the two-dimensional region by using outputs from said scanning means;

velocity profile forming means for forming a velocity profile by distributing the bloodstream velocities along a direction extending across the blood vessel;

blood vessel diameter calculating means for calculating a blood vessel diameter at each of different heartbeat time phases in one heartbeat cycle based on a distance between a rise and a fall of the velocity profile;

bloodstream volume calculating means for calculating a bloodstream volume based on the velocity profile sent from said velocity profile forming means and the blood vessel diameter sent from said blood vessel diameter calculating means and corresponding to a heartbeat time phase of the body to be examined; and display means for displaying the bloodstream volume.

33. An apparatus according to claim 32, further comprising means for controlling said scanning means so as to change a range of detectable maximum and minimum velocities of a bloodstream.

34. An apparatus according to claim 33, further comprising control means for changing the range of said scanning means in accordance with the heartbeat time phase of the body to be examined.

35. An apparatus according to claim 32, in which said velocity profile forming means includes means for smoothing the velocity profile.

36. An apparatus according to claim 32, in which said bloodstream volume calculating means calculates an average bloodstream volume by averaging bloodstream volumes continuously obtained.

37. An apparatus according to claim 36, in which said display means displays the average bloodstream volume and the bloodstream volume simultaneously.

38. An apparatus according to claim 32, in which said bloodstream volume calculating means calculates a stroke volume by adding bloodstream volumes obtained at different heartbeat time phases in one heartbeat cycle.

39. An apparatus according to claim 38, in which said bloodstream volume calculating means excludes a bloodstream volume having a negative polarity from an addition target for calculating the stroke volume.

40. An apparatus according to claim 38, in which said bloodstream volume calculating means calculates an average stroke volume by averaging stroke volumes which are repeatedly calculated over a plurality of heartbeat cycles.

41. An apparatus according to claim 40, in which said display means displays the stroke volume and the average stroke volume simultaneously.

42. An apparatus according to claim 32, in which said scanning means scans the two-dimensional region by shifting a timing in units of heartbeat cycles, and said bloodstream volume calculating means calculates a stroke volume by adding bloodstream volumes obtained at different heartbeat time phases that are repeatedly calculated over a plurality of heartbeat cycles.

43. An apparatus according to claim 42, in which said bloodstream volume calculating means excludes a bloodstream volume having a negative polarity from an addition target for calculating the stroke volume.

44. An apparatus according to claim 43, in which said bloodstream volume calculating means calculates an average stroke volume by averaging stroke volumes which are repeatedly calculated over a plurality of heartbeat cycles.

45. An apparatus according to claim 44, in which said display means displays the stroke volume and the average stroke volume simultaneously.

46. An ultrasonic diagnostic apparatus comprising:

scanning means for scanning a two-dimensional region including a blood vessel in a body with an ultrasonic wave;

bloodstream velocity calculating means for calculating bloodstream velocities at a plurality of positions in the two-dimensional region by using outputs from said scanning means;

velocity profile forming means for forming a velocity profile by distributing the bloodstream velocities along a direction extending across the blood vessel;

bloodstream volume calculating means for calculating a bloodstream volume from the velocity profile sent from said velocity profile forming means and a diameter of the blood vessel;

average bloodstream volume calculating means for calculating an average bloodstream volume by averaging bloodstream volumes continuously calculated by said bloodstream volume calculating means; and display means for displaying the bloodstream volume and the average bloodstream volume simultaneously.

47. An apparatus according to claim 46, further comprising means for controlling said scanning means so as to change a range of detectable maximum and minimum velocities of a bloodstream.

48. An apparatus according to claim 46, in which said control means changes the range of said scanning means in accordance with a heartbeat time phase of the body to be examined.

49. An apparatus according to claim 46, in which said velocity profile forming means includes means for smoothing the velocity profile.

50. An apparatus according to claim 46, in which said bloodstream volume calculating means calculates a stroke volume by adding the bloodstream volumes obtained at different heartbeat time phases in one heartbeat cycle.

51. An apparatus according to claim 50, in which said bloodstream volume calculating means excludes a bloodstream volume having a negative polarity from an addition target for calculating the stroke volume.

52. An apparatus according to claim 50, in which said bloodstream volume calculating means calculates an average volume by averaging stroke volumes which are continuously calculated over a plurality of heartbeat cycles.

53. An apparatus according to claim 52, in which said display means displays the stroke volume and the average stroke volume simultaneously.

54. An apparatus according to claim 46, in which said scanning means scans the two-dimensional region by shifting a timing in units of heartbeat cycles, and said bloodstream volume calculating means calculates a stroke volume by adding bloodstream volumes obtained at different heartbeat time phases that are continuously calculated over a plurality of heartbeat cycles.

55. An apparatus according to claim 54, in which said bloodstream volume calculating means excludes a bloodstream volume having a negative polarity from an addition target for calculating the stroke volume.

56. An apparatus according to claim 54, in which said bloodstream volume calculating means calculates an average volume by averaging stroke volumes which are continuously calculated over a plurality of heartbeat cycles.

57. An apparatus according to claim 56, in which said display means displays the stroke volume and the average stroke volume simultaneously.

* * * * *

UNITED STATES PATENT AND TRADEMARK OFFICE
CERTIFICATE OF CORRECTION

PATENT NO. : 5,515,857
DATED : May 14, 1996
INVENTOR(S) : Hiroyuki TSUJINO et al It is certified that error appears in the above-indentified patent and that said Letters Patent is hereby corrected as shown below:

Claim 1, Column 10, Line 67, after "and", insert
--forming a bloodstream velocity image;--.

Claim 1, Column 11, Line 10, after "vessel",
insert --,--.

Signed and Sealed this

Twenty-sixth Day of November 1996

Attest:

BRUCE LEHMAN

Attesting Officer

Commissioner of Patents and Trademarks